United States Patent
Ricketts

(10) Patent No.: US 6,544,539 B1
(45) Date of Patent: Apr. 8, 2003

(54) COMPOSITION AND METHOD FOR PRODUCING LUBRICATING, GERMICIDE FOAM

(75) Inventor: David J. Ricketts, Irvine, CA (US)

(73) Assignee: Devtech Marketing, Inc., Irvine, CA (US)

(*) Notice: Subject to any disclaimer, the term of this patent is extended or adjusted under 35 U.S.C. 154(b) by 0 days.

(21) Appl. No.: 10/077,269

(22) Filed: Feb. 16, 2002

Related U.S. Application Data

(63) Continuation-in-part of application No. 09/585,512, filed on Jun. 1, 2000, now Pat. No. 6,348,206, which is a continuation-in-part of application No. 09/406,039, filed on Sep. 27, 1999, now abandoned.

(51) Int. Cl.$^7$ ............................................. A01N 25/16
(52) U.S. Cl. ........................................ 424/405; 424/45
(58) Field of Search ................... 424/47, 405, 438, 424/672; 114/14.47, 651, 652, 673; 514/571, 738

(56) References Cited

U.S. PATENT DOCUMENTS

| | | | | |
|---|---|---|---|---|
| 5,534,266 A | * | 7/1996 | Ricketts | 424/672 |
| 5,720,984 A | * | 2/1998 | Ricketts | 424/672 |
| 5,722,350 A | * | 3/1998 | Marshall | 119/673 |
| 6,302,058 B1 | * | 10/2001 | Dahl et al. | 119/14.47 |
| 6,348,206 B1 | * | 2/2002 | Ricketts | 424/405 |

* cited by examiner

Primary Examiner—Michael G. Hartley
Assistant Examiner—Konata M. George
(74) Attorney, Agent, or Firm—Willie Kranite

(57) ABSTRACT

A method for producing a foam surfactant, and foam product suitable for a combined bovine teat dip and teat wash comprises air pressurization of a surfactant solution containing a germicide, disinfectant, biocide, etc., passing the air-surfactant mixture through a flow or line mixer to a foam holding cup adjacent the teat area and expanding the mixture to atmospheric in the holding cup to produce an adherent surfactant foam product with reduced run-off, which both protects and reduces infection of the teat, particularly at the teat canal and surrounding udder area.

43 Claims, 4 Drawing Sheets

COMPOSITION AND METHOD FOR PRODUCING LUBRICATING, GERMICIDE FOAM

Figure 1:
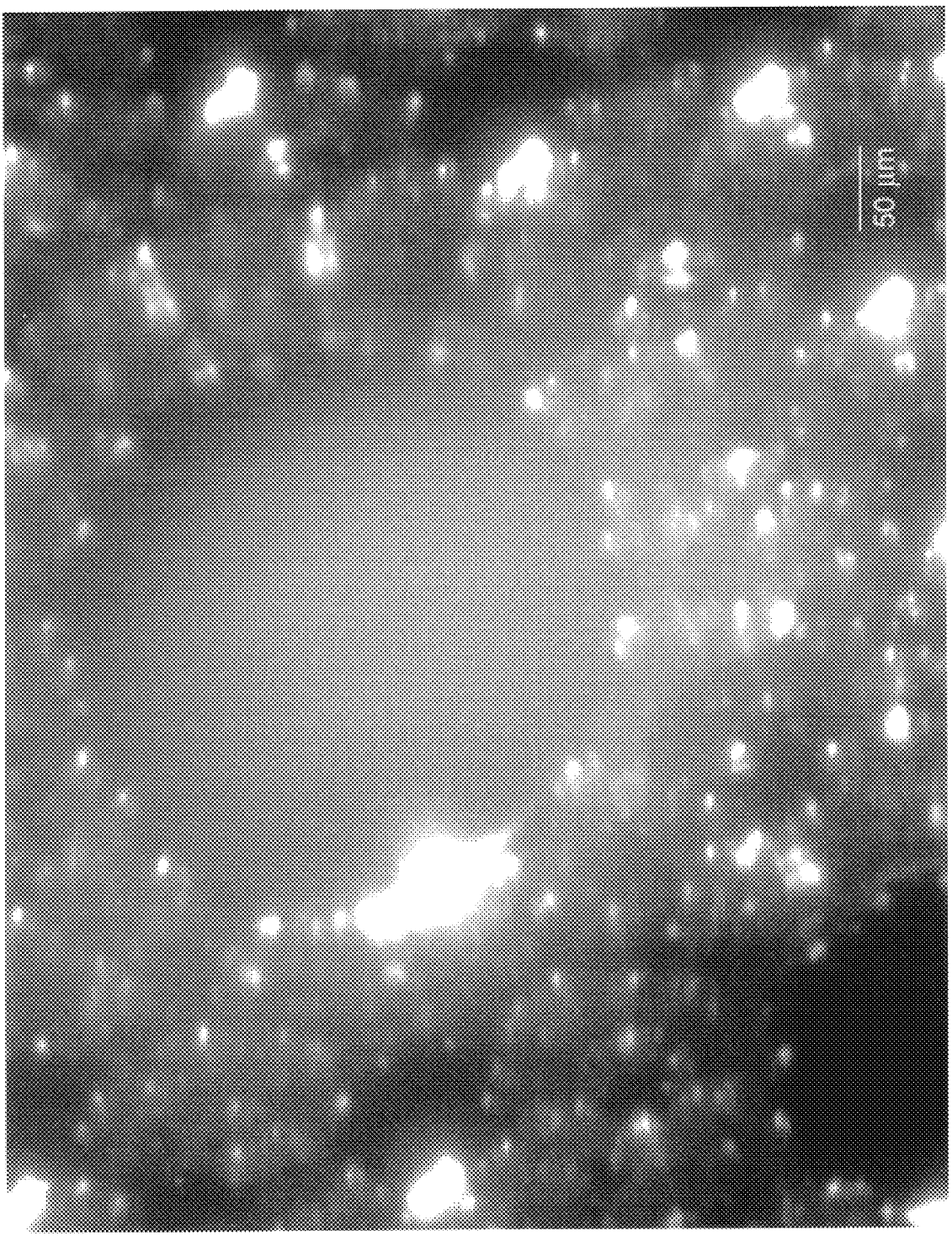

This application is a continuation-in-part of U.S. Ser. No. 09/585,512 filed Jun. 1, 2000 and issuing as U.S. Pat. No. 6,348,206 on Feb. 19, 2002, which is a continuation-in-part of U.S. Ser. No. 09/406,039 filed Sep. 27, 1999 and now abandoned.

BACKGROUND OF THE INVENTION

This invention relates to a new and improved foam for animal care such as bovine teat dips and teat washes, and the like.

Another object of this invention is to provide a new and improved combined foam teat dip and teat wash. Specifically, it would be highly desirable to provide a foamed bovine teat dip which would cover the outer teat area, and provide protection to the teat canal when the teat sphincter is open following a milking procedure, when the teat canal is exposed and highly vulnerable to immediate infection. Even when the teat sphincter has closed, it would still be desireable to prevent infection from reaching the area of the teat opening, and the teat area in general with reduced run off. This would enable the foam to adhere to and remain in close and protective contact with the teat. Further, it is desired to provide an apparatus with the capability of producing foam using a wide variety of surfactants, such as those disclosed, supra.

U.S. Pat. Nos. 3,713,423 and 4,305,346 describe an apparatus which coats a bovine teat area with fine spray or mist, but these patented devices are hand operated and do not produce any foam, let alone a foam fulfilling the above protective characteristics. It will also be appreciated that use of foam reduces the amount of liquid used for a bovine teat dip compared to either a spray or liquid dip, and hence an improvement in the operation of these two patents would be desirable.

THE INVENTION

According to the invention, there is provided a method for producing a combined foam teat dip and teat wash by pressurizing air with surfactant at a relatively high pressure followed by depressurization of the surfactant at atmospheric pressure to produce a foam which penetrates adherent dirt which can then be readily removed by cloths typically used by dairymen.

IN THE DRAWINGS

Figure 2:
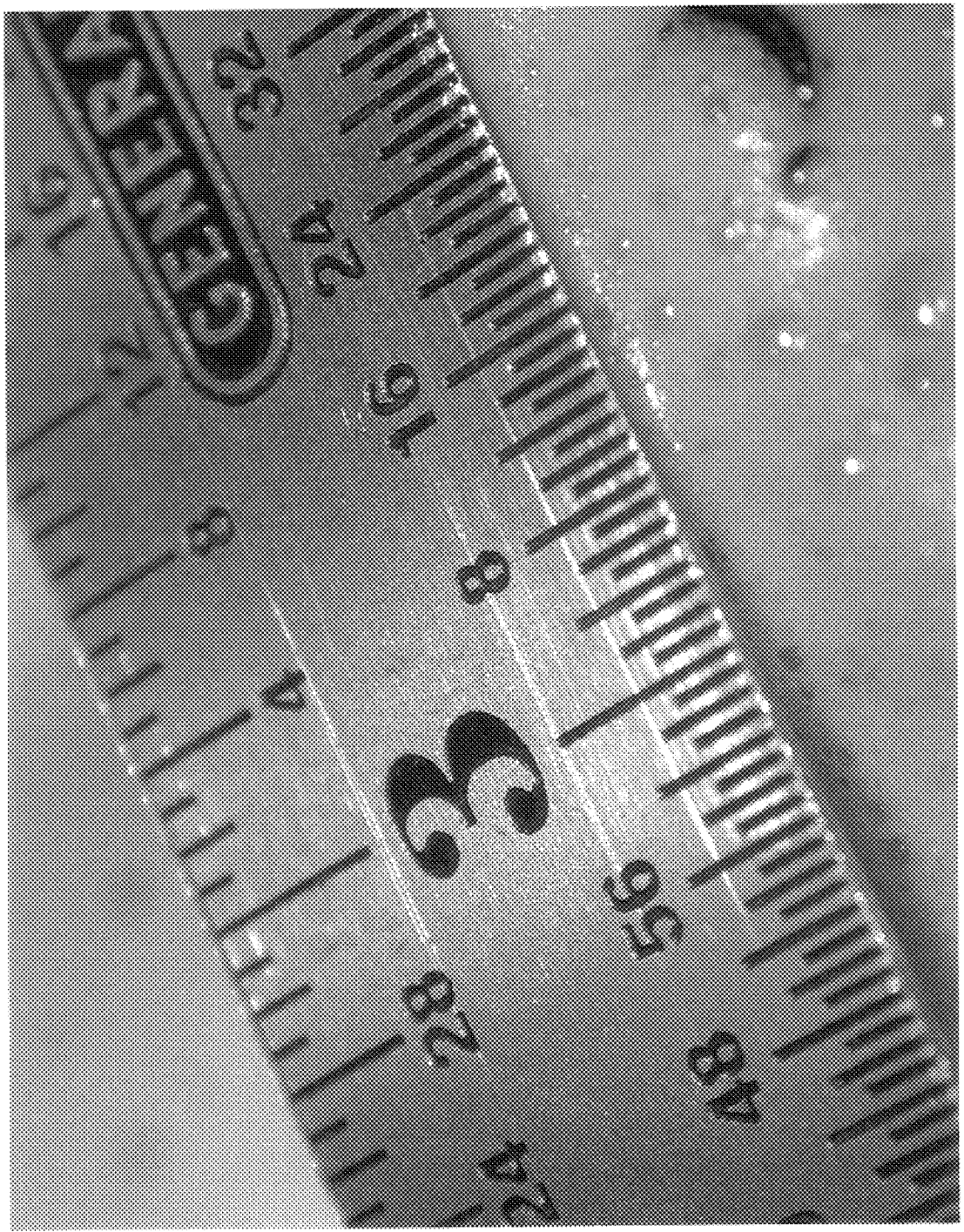
Figure 3:
Figure 4:

FIGS. 1 and 2 are photomicrographs showing the foam products of this invention at low and high magnifications; and, FIGS. 3 and 4 are photomicrographs showing the foam products of a commercial bovine foam teat dip at a low magnification.

The method for producing a foam, and the foam product therefrom for a combined post teat dip and pre milking teat wash comprises pressurizing a surfactant in a container with air, feeding the compressed air and surfactant to a flow or line mixer under turbulent flow conditions, and expanding the mixture of air and surfactant from an initial pressurized value, in the flow or line mixer through an open orifice and down to atmospheric pressure into a container cup surrounding the teat and adjacent udder area. A new and improved surfactant foam, or a mixture of surfactant and biocide is formed thereby which adheres to the teat, with reduced run off. Suitable types of equipment which may be employed to provide the method and foam product of this invention are disclosed in U.S. Pat. No. 6,302,058 and, U.S. Ser. No. 09/976,745 filed Oct. 13, 2001, incorporated herein by reference.

The foam of this invention is produced with a surfactant alone, or a mixture of surfactant and germicide, bactericide, and sufficient water, and pressuring the mixture with air ($CO_2$, nitrogen, propellant, etc.) to produce a lubricating, penetrating foam which may be used directly as a teat or udder wash, without pre-wetting, and following application the foam may be removed by wiping with a cloth.

If desired, in a larger use or industrial setting, particularly when used to produce a combined foam teat dip and teat wash, the container may be of larger size, and air is combined with the surfactant, or surfactant and mixture of germicide, etc., by pressure controlled air pumps. One type of equipment which may be modified to produce the desired type of foam is described in U.S. Pat. Nos. 3,713,423 and 4,304,346. The equipment described in these two patents employ a flow and mixing line for air and surfactant which is connected to the bottom entry of a teat cup, and a spray nozzle mounted at the entry. This equipment may be modified by removing the spray nozzle, thereby forming an open orifice in the teat cup. This modification enables a mixture of surfactant and air to be pressurized in the flow and mixing line. Upon depressurization to atmospheric at the open orifice, the desired quality of combined foam teat dip and teat wash is produced. This foam may then be used as an initial teat dip and a subsequent post dip. Typical flow and mixing line pressures vary from about 20–100 psi., and typical flow and mixing line lengths useful in milking operations are up to about 30 feet, and typically 20–30 feet.

The foam produced by the method of this invention is unique in terms of functioning as a combined bovine teat dip and after-milking teat wash since it adheres to the teat and udder area without significant run off, and forms a bead at the end of the teat. This area of the teat is at significant risk of infection both prior to and subsequent to milking, and the presence of the bead considerably reduces the possibility of infection. Also, since there is little foam run off, a longer period of protection is afforded against bacterial infection. Moreover, following cessation of milking, use of a post-dip which is not wiped off, enables fresh available liquid and foam to cover the teat end for about 8–12 minutes. This foam consistency provides sufficient time for the open teat end and teat canal to be covered by a foam bead when the teat sphincter is both open and closed, and hence when the teat canal is at a high risk of infection.

The foam produced by the method of this invention ia shown in FIGS. 1 and 2 were digitally photographed with a close focus, high resolution Nikon digital camera and a long focus microscope attached to a computer that captured the images in digital mode. The microscopic images were captured by taking a thin slice of foam and back lighting with a high intensity light to overcome the opacity of iodine germicide used in the teat dip which was contained in the foam. The surfactant used in these photographs is described in Applicant's patents, infra.

The micron size of the spherically formed bubbles was determined by taking an image of a fifty micron wire at the same focus as the bubble images and transferring this measured size distance to the photomicrographs, shown by the fiducial marking. Since it was not feasible to photograph the foam as it was being formed, the images were made with delay from 45 seconds to several minutes.

The size of the newly formed foam bubbles was measured and photographed as between 5–200 microns in diameter, and preferably below 200 microns in diameter, the bulk of the bubbles being close to about 50 microns in size. While some of the bubbles (about 15%) in these photographs are greater than 200 microns, they were either formed by an imbalance of air with the liquid flow, or formed by the bubbles joining together over time. The bubbles contained in the liquid matrix are at a higher pressure than atmospheric, and the foam is characterized as being a liquid with spherical air bubble inclusions, without walls, a wall being defined as having inner and outer surfaces. The foam itself is best described as being "stiff".

Pressure exceeding atmospheric within the bubbles was calculated using the surface tension of the iodine teat dip which was used when obtaining the microphotographs, the pressure becoming greater as the bubble diameter decreases. This pressure can be calculated by the formula: P (inside bubble)=P(outside bubble)+2×(surface tension)/bubble radius, and is measured at a solution surface tension of 32 dynes/cm. (The surface tension of pure water is 70 dynes/cm.).

Hence, the pressure difference across the bubble is therefore inversely proportional to the bubble size. Accordingly, the pressure inside a 15 micron bubble is 2.4 psi above ambient pressure (14.6 psi) and a visual observation of a 5 micron bubble size would calculate to an internal pressure of about 7.2 pounds higher than atmospheric. Since the maximum resolution of the long focus microscope is 4 microns, if bubbles of 1 micron were formed at the actual time of foam generation, they would have internal pressures of about 36 psi over atmospheric, and this would obviously account for the stiffness and persistence of the foam.

By contrast, bubbles produced by equipment described in U.S. Pat. No. 5,722,350 (i.e., FIGS. 3 and 4) produced bubbles having a size range of about 600–1200 microns. The differential internal bubble pressure of about 2.4/40=0.06 psi, is low enough that result in the bubbles sharing common walls and appear to be hexagonally-shaped, rather than the much smaller, spherical bubbles produced by this invention. This would account for the "loose" type of relatively short lasting foam produced by the equipment of that patent.

In addition to those surfactants described in McCutcheon's publications, surfactants which may be useful in the foams of this invention are described in U.S. Pat. Nos. 2,977,315; 3,950,544; 4,049,830; 4,258,056; 4,371,517; 4,671,958; 4,678,668; 4,940,702; 5,028,427; 5,175,160; 5,208,257; 5,466,959 (PVP); U.S. Pat. No. 5,529,770 ($C_{16-18}$ fatty alcohols); U.S. Pat. No. 5,616,348 (polyethoxylated polyoxypropylene block copolymer—POLOXAMER); and German Patent 2,936,934, incorporated herein by reference. Also useful surfactants are 9–12 mole ethoxylated alkyl phenols; nonyl phenoxy polyethoxy ethanol surfactant; and, non-ionic fatty alcohol polyglycol ether carboxylic acid.

Surfactants such as polyethenoxy detergents and $I_2$ are disclosed in an article by Benjamin Carroll in the Journal of Bacteriology, 69: 413–417, (1955) are useful as foams.

Commercial surfactants containing iodine which are known for use as teat dip formulations include 9–12 mole ethoxylated phenols. A surfactant of this type is sold by Norman Fox & Co. under the trade name of NORFOX N-P9, and listed in "McCutcheon's Emulsifiers and Detergents", (1989 and 1994) specifically for use with iodophors. Another type of teat dip is sold by Klenzade™ Teat Guard, and contains a nonyl phenoxypolyethoxy ethanol surfactant having 1% titratable iodine. Both of these surfactants may also be used in the foam product of this invention, provided they comply with existing regulations. However, producers, distributors and users of nonyl phenoxy surfactants should be continually aware of ongoing regulations governing the use of specific surfactants in this category when used for bovine teat dips due to possible mutagenic effects of a given surfactant.

Applicant's U.S. Pat. Nos. 5,720,984 and 5,534,266 describe a non-ionic, fatty alcohol polyglycol ether carboxylic acid and sold under the trade names of AKYPO™RLM-45, AKYPO™RLM-100, AKYPO™RLM-160, and mixtures thereof, the preferred composition being AKYPO™RLM-100 (Chemical Abstracts Registry 74349-89-6). As noted in these Applicant's patents, supra, the herd life of cows varies from about 3–7 years, but there has been no noticeable reduction in herd life in the approximate 2.5 years since the product has been in use.

Patents which relate either directly or indirectly to foam or defoamers in connection with bovine teat dips are disclosed in U.S. Pat. Nos. 2,989,434; 4,945,110; 5,063,249; 5,370,815; 5,575,993; 5,722,350; 5,843,912; and, 5,967,202. European Patent 077,2973; and, French Patent 2,633,308 also describe bovine teat dip foams.

Germicides or bactericides which may be employed in the foams of this invention include: chlorhexidine, $I_2$, iodides such as $I^-$, HI, or equivalent (e.g., KI, NaI, $CaI_2$, etc.), iodophors, etc., chlorine dioxide, quaternary ammonium compounds, etc.

The amount of water employed in the foam compositions of this invention is typically about 78%–95% by weight, and this enables a sufficient dilution of the germicide in the foam to reduce the amount required and satisfy USDA and FDA requirements for the content of sanitizers, due inter alia to the penetrating capabilities of the foam.

What is claimed is:

1. A combined foam bovine teat and udder dip, and after milking post teat dip and udder wash formed by admixing a surfactant, water and a bacteria control agent with pressurized air in a flow and line mixer and subsequently depressurizing the admixture from an initial pressurized value in the flow and line mixer down to atmospheric pressure and into an open orifice in a connected teat cup surrounding the teat and adjacent udder area, the consistency of the foam being sufficient to apply penetrating and adherent foam to the teat and adjacent udder area for an effective contact time prior to milking, and without significant run-off, thereby enabling ready removal of deleterious material therefrom; and if desired, following cessation of milking the post teat dip and after milking and udder wash which is not wiped off enables the teat including the teat end, for a sufficient length of contact time, thereby causing fresh available liquid and foam to cover the teat end, and hence the teat canal opening with foam when the teat sphincter muscle is both open and closed, and thereby reduce the possibility of infection through the teat canal.

2. The combined foam and teat dip of claim 1, in which the water content of the foam is about 78%–95% by weight.

3. The combined foam and teat dip of claim 1, comprising bubbles contained in a liquid matrix, the pressure inside a bubble being greater than atmospheric, and the foam being characterized as being a liquid with spherical air bubble inclusions, without walls.

4. The combined foam and teat dip of claim 1, in which the bubble size is preferably below about 200 microns in diameter.

5. The combined foam and teat dip of claim 1, in which the bubbles have a size range of about 5–200 microns in diameter.

6. The combined foam and teat dip of claim 1, in which the flow and mixing line pressures are at least 20 psi.

7. The combined foam and teat dip of claim 1, in which the flow and mixing line pressures vary up to about 100 psi.

8. The combined foam and teat dip of claim 1, in which the flow and mixing line lengths are up to about 30 feet.

9. The combined foam and teat dip of claim 1, in which the flow and mixing line lengths are about 20–30 feet.

10. The combined foam and teat dip of claim 1, in which the flow and mixing line lengths are up to about 30 feet and the flow and mixing line pressures are greater than about 20 psi.

11. A combined foam teat and udder dip, and after milking post teat dip and udder wash formed by admixing a surfactant, water and a bacteria control agent with pressurized air under turbulent flow conditions and subsequently depressurizing the admixture from an initial pressurized value down to atmospheric pressure into an open orifice in a connected teat cup surrounding the teat and adjacent udder area, the consistency of the foam being sufficient to apply penetrating and adherent foam to the teat and surrounding udder area for an effective contact time prior to milking, and without significant run-off, thereby enabling ready removal of deleterious material therefrom; and if desired, following cessation of milking, the post teat dip and after milking and udder wash which is not wiped off enables the foam to adhere to the teat including the teat end, for a sufficient length of contact time, thereby causing fresh available liquid and foam to cover the teat end, and hence the teat canal opening with foam when the teat sphincter muscle is both open and closed, and thereby reduce the possibility of infection through the teat canal.

12. The foam teat and udder wash of claim 11, comprising bubbles contained in a liquid matrix, the pressure inside a bubble being greater than atmospheric, and the foam being characterized as being a liquid with spherical air bubble inclusions, without walls.

13. The foam teat and udder wash of claim 11, in which the flow and mixing line pressures are at least 20 psi.

14. The foam teat and udder wash of claim 11, in which the flow and mixing line pressures vary up to about 100 psi.

15. The foam teat and udder wash of claim 11, in which the flow and mixing line lengths vary up to about 30 feet.

16. The foam teat and udder wash of claim 11, in which the flow and mixing line pressure is at least 20 psi, and the flow and mixing line lengths vary up to about 30 feet.

17. The foam teat and udder wash of claim 11, in which the water content of the foam is about 78%–95% by weight.

18. The foam teat and udder wash of claim 1, in which the germicide is selected from the class consisting of $I_2$, $I^-$, HI and, iodophors; chlorine dioxide; chlorhexidine; quaternary ammonium compounds; and, hexachlorophene.

19. The foam teat and udder wash of claim 11, in which the germicide is selected from the class consisting of $I_2$, $I^-$, HI and, iodophors; chlorine dioxide; chlorhexidine; quaternary ammonium compounds; and, hexachlorophene.

20. The foam teat and udder wash of claim 1, in which the surfactant is selected from the class consisting of PVP; $C_{16}$–$C_{18}$ fatty alcohols; polyethoxylated polyoxypropylene block copolymer; 9–12 mole ethoxylated alkyl phenols; nonyl phenoxy polyethoxy ethanol surfactant; and, non-ionic fatty alcohol polyglycol ether carboxylic acid.

21. The foam teat and udder wash of claim 11, in which the surfactant is selected from the class consisting of PVP; $C_{16}$–$C_{18}$ fatty alcohols; polyethoxylated polyoxypropylene block copolymer; 9–12 mole ethoxylated alkyl phenols; nonyl phenoxy polyethoxy ethanol surfactant; and, non-ionic fatty alcohol polyglycol ether carboxylic acid.

22. A combined foam bovine teat dip and after milking post teat dip formed by admixing a surfactant, liquid and a bacteria control agent with pressurized gas in a flow and line mixer and subsequently depressurizing the admixture from an initial pressurized value in the flow and line mixer down to atmospheric pressure and into an open orifice in a connected teat cup surrounding the teat area, the consistency of the foam being sufficient to apply penetrating and adherent foam to the teat for an effective contact time prior to milking, and without significant run-off, thereby enabling ready removal of deleterious material therefrom; and if desired, following cessation of milking the post teat dip and after milking wash which is not wiped off enables the foam to adhere to the teat including the teat end, for a sufficient length of contact time, thereby enabling fresh available liquid and foam to cover the teat end, and hence the teat canal opening with foam when the teat sphincter muscle is both open and closed, and thereby reduce the possibility of infection through the teat canal.

23. The product of claim 22, in which the foam contacts an udder surface adjacent a teat.

24. The product of claim 22, in which the flow and line mixer is attached to the connected teat cup and to a flow control means.

25. The product of claim 22, in which the pressure in the flow and line mixer exceeds about 20 psi.

26. The product of claim 22, characterized by a stiff foam providing bubble inclusions without walls inside a matrix of liquid, the bubble sizes varying from mainly about 5–200 microns.

27. The product of claim 26, in which the liquid content of the foam varies from about 78%–95% by weight.

28. The product of claim 26, in which the foam provides a consistency sufficient to cover the teat for at least about 8 minutes.

29. The product of claim 27, in which the surfactant is a non-ionic, fatty alcohol, polyglycol ether carboxylic acid.

30. The product of claim 22, in which the bacteria control agent comprises a germicide selected from the class consisting of $I_2$, I, $HI^-$ and iodophors; chlorine dioxide; chlorhexidine; quaternary ammonium compounds; and, hexachlorophene.

31. The product of claim 22, in which the surfactant is selected from the class consisting of PVP; $C_{16}$–$C_{18}$ fatty alcohols; polyethoxylated polyoxypropylene block copolymer; 9–12 ethoxylated alkyl phenols; and, nonyl phenoxy polyethoxy ethanol surfactant.

32. A method of producing a combined foam teat and after milking post teat dip formed by admixing a surfactant, liquid and a bacteria control agent with gas under pressure in a flow and line mixer and subsequently depressurizing the admixture from an initial pressurized value in the flow and line mixer down to atmospheric pressure, and into an open orifice in a connected teat cup surrounding the teat, the consistency of the foam being sufficient to apply penetrating and adherent foam to the teat for an effective contact time prior to milking, and without significant run-off, thereby enabling ready removal of deleterious material therefrom; and, if desired, following cessation of milking, the post teat dip and after milking wash which is not wiped off enables the foam to adhere to the teat, including the teat end, for a sufficient length of contact time, thereby causing fresh available liquid and foam to cover the teat end, and hence the teat canal opening with foam when the teat sphincter muscle is both open and closed, and thereby reduce the possibility of infection through the teat canal.

33. A combined foam bovine teat dip and after milking post teat dip, characterized as being a stiff foam providing gas bubble inclusions without walls inside a matrix of surfactant and liquid, the consistency of the foam being sufficient to penetrate deleterious material on the teat for an effective contact time prior to milking, and without significant run-off, thereby enabling ready removal of the deleterious material therefrom; and if desired, following cessation of milking, the post teat dip and after milking wash which is not wiped off enables the foam to adhere to the teat including the teat end, for a sufficient length of contact time, thereby enabling fresh available liquid and foam to cover the teat end, and hence the teat canal opening with foam when the teat sphincter muscle is both open and closed, and thereby reduce the possibility of infection through the teat canal.

34. The product of claim 33, in which the gas bubble sizes vary mainly from about 5–200 microns.

35. The product of claim 33, in which the liquid content of the foam varies from about 78%–95% by weight.

36. The product of claim 33, in which the foam consistency is sufficient to cover the teat for about at least 8 minutes.

37. The product of claim 33, in which the gas bubble size of the foam varies from about 5–200 microns, the liquid content of the foam varies from about 78%–95% by weight, and the foam consistency is sufficient to cover the teat for about at least 8 minutes.

38. The product of claim 33, in which the gas bubble size of the foam varies from mainly about 5–200 microns, and the liquid content of the foam varies from about 78%–95% by weight.

39. The product of claim 33, in which the gas bubble size of the foam varies from mainly about 5–200 microns, and the foam consistency is sufficient to cover the teat for about at least 8 minutes.

40. The product of claim 33, in which the liquid content of the foam varies from about 78%–95% by weight, and the foam consistency is sufficient to cover the teat for about at least 8 minutes.

41. The product of claim 33, in which the surfactant is a non-ionic fatty alcohol, polyglycol ether carboxylic acid.

42. The product of claim 33, in which the bacteria control agent comprises a germicide selected from the class consisting of $I_2$, I, $HI^-$, and iodophors; chlorine dioxide; chlorhexidine; quaternary ammonium compounds; and, hexachlorophene.

43. The product of claim 33, in which the surfactant is selected from the class consisting of PVP; $C_{16}$–$C_{18}$ fatty alcohols; polyethoxylated polyoxypropylene block copolymer; 9–12 ethoxylated alkyl phenols; and, nonyl phenoxy polyethoxy ethanol surfactants.

* * * * *